United States Patent [19]

Hepher et al.

[11] Patent Number: 5,056,355

[45] Date of Patent: Oct. 15, 1991

[54] DUST MONITORS AND DUST MONITORING

[75] Inventors: Michael J. Hepher, Coylton; Jonathan N. Hides, Glasgow, both of Scotland

[73] Assignee: Murgitroyd & Company, Glasgow, England

[21] Appl. No.: 444,734

[22] Filed: Dec. 1, 1989

[30] Foreign Application Priority Data

Dec. 3, 1988 [GB] United Kingdom ............... 8828277

[51] Int. Cl.$^5$ ...................... G01N 15/02; G01N 29/02
[52] U.S. Cl. .................................. 73/24.03; 73/24.06; 73/28.05
[58] Field of Search ................. 73/24.06, 24.01, 24.03, 73/24.05, 28.01, 28.04, 28.05, 28.06

[56] References Cited

U.S. PATENT DOCUMENTS

| | | | |
|---|---|---|---|
| 3,164,004 | 1/1965 | King, Jr. .............................. | 73/24.06 |
| 3,260,104 | 7/1966 | King, Jr. .............................. | 73/24.06 |
| 3,561,253 | 2/1971 | Dorman .......................... | 73/28.05 X |
| 3,653,253 | 4/1972 | Olin .................................... | 73/24.03 |
| 3,715,911 | 2/1973 | Chuan .............................. | 73/28.05 X |
| 4,561,286 | 12/1985 | Sekler et al. ......................... | 73/24.06 |

*Primary Examiner*—Hezron E. Williams
*Assistant Examiner*—Joseph W. Roskos
*Attorney, Agent, or Firm*—Ratner & Prestia

[57] ABSTRACT

A dual monitor comprises a piezoelectric sensor in the form of a quartz crystal and an electrode system thereon. An exposure device in the form of a dust discriminator is provided to expose the piezoelectric sensor at least periodically to a stream of a gas which may contain dust or other organic or inorganic particulate material whose presence in or absence from the gas is to be monitored. The gas of said stream consists primarily of air. An electronic monitoring device is provided coupled to the electrode system of said piezoelectric sensor to monitor variations in the resonant frequency of said piezoelectric sensor induced by the aggregation of dust or other particulate material on said piezoelectric sensor.

3 Claims, 7 Drawing Sheets

_Fig.13_   _Fig.14_

_Fig.15_

DUST MONITORS AND DUST MONITORING

This invention relates to dust monitors and to dust monitoring, and more particularly but not exclusively to real-time dynamic monitoring of gas-borne dust by use of a dust monitor based on a piezoelectric sensor.

BACKGROUND OF THE INVENTION

There are numerous circumstances where health, safety, and/or product quality can be affected by gas-borne or air-borne dusts or micro-organisms. Accordingly there exists a requirement for a method and apparatus enabling rapid and accurate monitoring of dusts or micro-organisms, preferably with selectivity in respect of the range of size or type of air-borne particulate that is monitored, and it is an object of the invention to provide such a method and apparatus.

SUMMARY OF THE INVENTION

According to a first aspect of the present invention there is provided a dust monitor comprising a piezoelectric sensor including a piece of piezoelectric material and an electrode system thereon, and exposure means to expose the piezoelectric sensor at least periodically to a stream of a gas which may contain dust or other organic or inorganic particulate material whose presence in or absence from the gas is to be monitored. The gas of said stream may consist primarily or substantially entirely of air. The piezoelectric material may comprise a crystalline material, for example quartz, or the piezoelectric material may comprise a non-crystalline material, for example polyvinylidene difluoride (PVDF). The electrode system may comprise two electrodes of suitable shape, size, and mutual spacing, preferably leaving at least one piezo-resonant area of the sensor to be exposed to the dust or the particulate material. The dust monitor preferably further comprises electronic circuit means coupled to the electrode system of said piezoelectric sensor to monitor variations in the resonant frequency of said piezoelectric sensor induced by the aggregation of dust or other particulate material on said piezoelectric sensor.

The exposure means preferably operates on a cyclic basis to expose the piezoelectric sensor periodically to said stream of gas, said exposure means comprising or being associated with a sensor cleaning system operable between periods of exposure of said sensor to said stream of gas substantially to remove dust or other particulate material aggregated on said piezoelectric sensor during a preceding period of exposure. The exposure means preferably operates to isolate said piezoelectric sensor from said stream of gas between said periods of exposure to facilitate operation of the sensor cleaning system.

The sensor cleaning system may comprise a vacuum system or an air jet system in the case of a piezoelectric sensor monitoring the dust or other particulate material by means of the gravity effect and/or the perturbation effect; the sensor cleaning system may comprise an electrostatic charge reversal system where the piezoelectric sensor is a charged crystal systems; where the piezoelectric sensor is coated with a binder material for binding of the dust or other particulate material to be monitored during said periods of exposure, the sensor cleaning system may comprise means for washing the sensor with a binder solvent, and for subsequently re-coating the piezoelectric sensor with clean binder.

The exposure means may comprise a cyclone or other dust size discriminator to cause substantially only particles on one size of a predetermined size limit to reach the piezoelectric sensor (i.e. to limit exposure of the piezoelectric sensor to particulates which are either above or below the size limit); the cyclone is preferably such that the piezoelectric sensor is exposed substantially only to particles of respirable size (less than a nominal 8 micrometer size) while dust particles which may have a nuisance value but are larger than the nominal respirable limit of 8 micrometers are caused substantially to be diverted away from the piezoelectric sensor to a second piezoelectric sensor.

The dust monitor preferably incorporates temperature stabilisation means thermally coupled to the piezoelectric sensor and operable to tend to stabilise the temperature of the sensor during operation of the dust monitor. The temperature stabilisation means may comprise means to supply a stream of temperature-controlled air to a portion of the piezoelectric sensor other than the portion or portions of the piezoelectric sensor exposed to the stream of gas whose particulate content is to be monitored. Alternatively, the temperature stabilisation means may comprise a Peltier pile thermally coupled to the piezoelectric sensor and supplied in use with current of a magnitude and polarity such as to stabilise the temperature of the piezoelectric sensor to within a predetermined range of temperatures, preferably as measured by a thermocouple also thermally coupled to the piezoelectric sensor. Said electronic circuit means coupled to the electrode system of the piezoelectric sensor may comprise an oscillator having an oscillatory frequency wherein the variations in oscillatory frequency are substantially or entirely determined by the variations in the resonant frequency of the piezoelectric sensor as brought about by the aggregation of dust or other particulate material thereon, and frequency variation sensing means to sense the variations in oscillatory frequency. The frequency variation sensing means may comprise a frequency-to-voltage converter (optionally fed through a fixed-ratio frequency divider) and a threshold crossing detector operable to give an output signal if the frequency variation exceeds a predetermined limit, for example, to give an alarm signal if the sensed frequency variation indicated a concentration of gas-borne or air-borne dust or other particulate material in excess of a predetermined limit.

For the monitoring of air-borne organic particulates of a biological nature, the piezoelectric sensor may be coated with an agar rich in nutrients to encourage growth of a particular analyte micro-organism, or alternatively, the piezoelectric sensor may be coated with a material which reacts directly with a side product chemically related to a specific organism.

According to a second aspect of the present invention there is provided a method of dust monitoring for monitoring the presence in or absence from a gas of dust or other organic or inorganic particulate material, said method comprising the steps of periodically applying a stream of said gas to the piezoelectric sensor of a dust monitor in accordance with the first aspect of the present invention, and monitoring variations in the resonant frequency of said piezoelectric sensor induced by the aggregation of dust or other particulate material on said piezoelectric sensor.

Preferably said method includes the further steps of periodically discontinuing application of the stream of gas to said piezoelectric sensor, and of removing any dust or other particulate material aggregated on said piezoelectric sensor prior to the next period of application of the stream of gas to said piezoelectric sensor.

Preferably said method also includes the step of subjecting the dust or other particulate material in said gas to discrimination based on particle size such as to cause said stream of gas to contain substantially only particles either above or below a predetermined nominal size; more preferably the method comprises limiting exposure of said piezoelectric sensor to particulate material of a respirable size. Preferably, the monitoring of variations in the resonant frequency of the piezoelectric sensor is such as to cause an alarm or other signal indicative of the gas being monitored containing more than a predetermined maximum amount of respirable particles.

Said method way also include the steps of applying heat to or withdrawing heat from the piezoelectric sensor in a manner such as to tend to stabilise the temperature of the piezoelectric sensor during dust monitoring.

BRIEF DESCRIPTION OF THE DRAWINGS

Embodiments of the invention will now be described by way of example, with reference to the accompanying drawings wherein:

FIG. 1 is a schematic diagram of a first embodiment of the invention;

FIG. 2 is a schematic diagram of a second embodiment of the invention;

FIGS. 3A and 3B are respectively schematic and perspective diagrams of a third embodiment of the invention;

FIGS. 4A and 4B are respectively schematic and perspective diagrams of a fourth embodiment of the invention;

FIGS. 5A and 5B show two variations in an application of the invention;

FIG. 6 is a schematic section of a fifth embodiment of the invention;

FIG. 7 is a schematic section of a sixth embodiment of the invention;

FIG. 8 is a schematic section of a seventh embodiment of the invention;

FIG. 9 is a schematic diagram of a computerised dust monitoring system;

FIG. 10 is a dual graph of measurements obtained in testing of the invention;

FIG. 11 is a block schematic diagram of an electronic circuit for use in the invention;

FIG. 12 is a detailed diagram of the circuit of FIG. 11;

FIG. 13 is a perspective diagram of a device of the invention incorporating a leveling device;

FIG. 14 is a schematic detail diagram of the device of FIG. 13 and

FIG. 15 is a schematic diagram of a dust monitor device in accordance with the present invention.

DESCRIPTION OF PREFERRED EMBODIMENTS

Before referring to the drawings in detail, some theoretical principles underlying the invention will first be discussed. A piezoelectric material such as quartz or polyvinylidene difluoride (PVDF) has the property of converting mechanical strain to electricity, and vice versa. An electrode system, such as a suitably dimensioned pair of electrodes, on a suitably dimensioned piece of piezoelectric material enable measurement of strain-induced voltages and/or application of an electrostatic field to induce mechanical strain. Such a piezoelectric device can form the frequency-determining resonant element in an electronic oscillator circuit. If part of the surface of such a piezoelectric device is exposed to accretion of dust or other particulate material, the mass increment decreases the resonant frequency in accordance with the Sauerbrey equation, as follows:

$$DF = -Dm \cdot F/R \cdot t \cdot A$$

where

DF is the frequency change in Hertz,

Dm is the mass change in microgrammes,

F is the resonant frequency of the clean (dust-free) piezoelectric device in Megahertz, R is the density of the piezoelectric material in grammes per cubic centimeter, t is the thickness of the piezoelectric device in centimeters, and A is the area of the piezoelectric device exposed to dust, in square centimeters.

Thus a suitable piezoelectric device can be employed as a piezoelectric sensor for sensing the accretion on the sensor of dust of other particulate material, the mass of the particulate material being readily measurable by determining the changes in the resonant frequency of the piezoelectric sensor, or by any other suitable technique.

Measurement can be made of the rate of deposition (mass increment per unit time) of dust on the piezoelectric sensor, or measurement can be made of the total accumulation of dust on the piezoelectric sensor over a fixed sampling period (for example, a predetermined number of seconds or minutes), or any suitable combination of both such types of measurement can be employed. The piezoelectric sensor is preferably cleaned between successive ones of these measuring periods of sampling periods.

In the following description of specific embodiments of the invention, the preferred piezoelectric sensor is a piezoelectric quartz crystal with a pair of electrodes thereon and with at least one area on one or both sides of the crystal exposed to allow dust or other particulate material to accumulate thereon in a manner which affects the resonant frequency of the crystal. Accordingly, references to a crystal are to be taken as referring to a crystalline piezoelectric dust sensor, but it should be borne in mind that suitable non-crystalline piezoelectric sensors may be substituted in appropriate circumstances. The preferred piezoelectric crystal sensor is an AT-cut quartz crystal with a diameter of about 1.3 centimeters and a thickness of about 180 micrometers, having electrodes formed of gold or silver, and a resonant frequency of 9 MHz. Alternatively a GT-cut quartz crystal may be used as it has been found that such crystals have virtually no temperature coefficient in the range 0 degree C. to 40 degrees C.

For the sake of simplicity FIGS. 1 to 8 (detailed below) show dust sampling systems without the external electronic circuitry enabling resonant frequency measurements to be performed on the piezoelectric sensor crystal within the sampling system to complete the dust monitoring system and function. Moreover, FIGS. 1 to 6 omit the sensor cleaning systems that would normally be necessary in practice.

Referring now to FIG. 1, a piezoelectric sensor crystal 20 hangs freely in a horizontal position within a sampling cell 22. Air (or another gas) which may contain suspended particulate material is fed into the sampling cell 22 through an upper inlet duct 24, circulates through the cell 22, and is finally exhausted from the sampling cell 22 through a lower outlet duct 26. A representative aliquot of the air-borne particulate material aggregates on the sensor crystal 20. Either the rate of aggregation is measured as the decline with time of the apparent resonant frequency of the crystal 20, or the total aggregation is measured at the end of fixed sampling period as the decrement of the apparent resonant frequency of the crystal 20.

Figure 1:
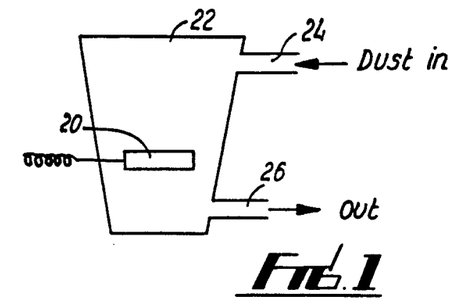

After each sampling period, the sensor crystal 20 is blown, vacuumed, shaken, or washed substantially clean of collected particulates in preparation for a subsequent sampling session. Air flow through the sampling cell 22 is preferably cut off during cleaning of the crystal 20.

Figure 2:
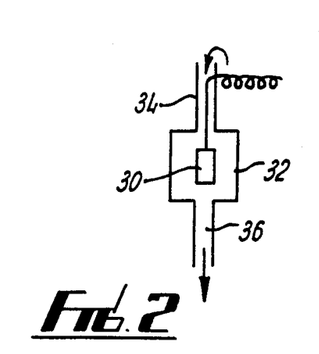

In FIG. 2, a piezoelectric sensor crystal 30 hangs freely in a vertical position within a sampling chamber 32 having an supper inlet duct 34 and a lower outlet duct 36. The dust sampling system of FIG. 2 functions in a generally similar manner to that described above with respect to FIG. 1.

Figure 3A:
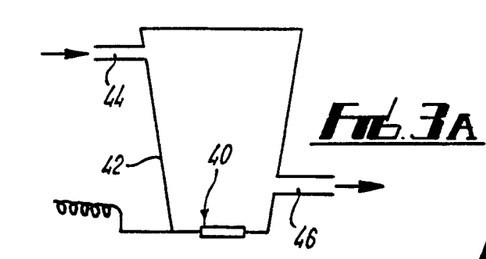
Figure 3B:
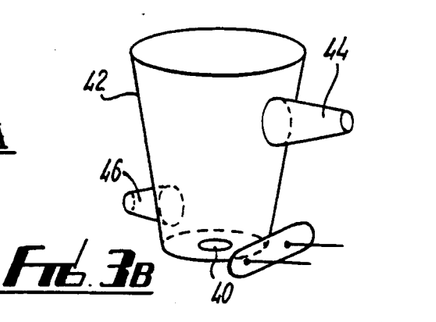

The dust sampling system of FIG. 3A is in some respects similar to that of FIG. 1, but differs in that the piezoelectric sensor crystal 40 of the FIG. 3 system is an integrated rim-bound crystal forming part of the inner surface of the sampling chamber 42, as is more clearly shown in the perspective schematic of FIG. 3B. Also shown in FIG. 3B are the cross-sectional tapers and radial offsets of the upper inlet duct 44 and the lower outlet duct 46 to give requisite gas and particulate flow conditions within the sampling chamber 42.

Figure 4A:
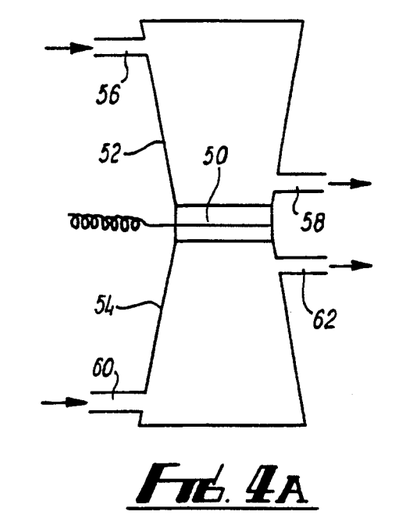
Figure 4B:
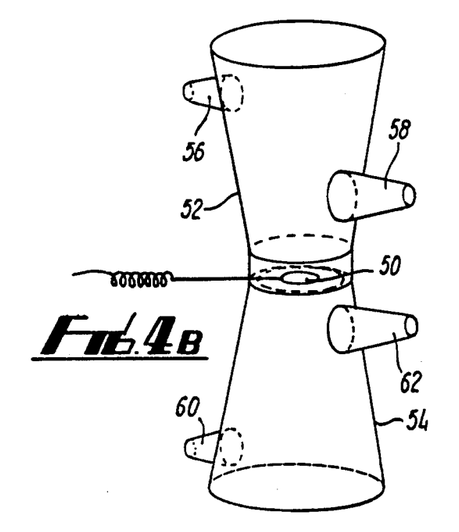

The double-chamber bifunctional dust sampling system shown in FIG. 4A (diagramatic) and FIG. 4B (perspective schematic) is an extension of that shown in FIGS. 3A and 3B, in that the piezoelectric sensor crystal 50 divides the system into an upper chamber 52 and a lower chamber 54 which are mutually pneumatically isolated. The upper chamber 52 has an upper inlet duct 56 and a lower outlet duct 58 (corresponding to the inlet and outlet ducts 44 and 46 of the FIG. 3 system), while the lower chamber 54 has a lower inlet duct 60 and an upper outlet duct 62.

The upper chamber 52 in the FIG. 4 system performs the same function as the dust sampling chamber 42 in the FIG. 3 system. The lower chamber 54 of the FIG. 4 system can be used to carry heated air for temperature control of the sensor crystal 50. Alternatively, in the case where the face of the crystal 50 exposed to the interior of the upper chamber 52 is coated with a binder to promote adherence of particulate material on the sensitive area of the piezoelectric sensor, the face of the crystal 50 exposed to the interior of the lower chamber 54 may also be coated with binder, and preferably also exposed to a current of clean air generally matching the current of air through the upper chamber 52. This procedure will differentially back off base-line drift in binder-type dust monitoring systems.

Figure 5A:
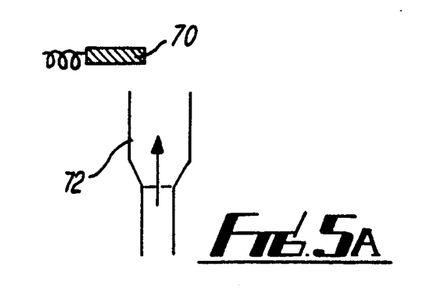
Figure 5B:
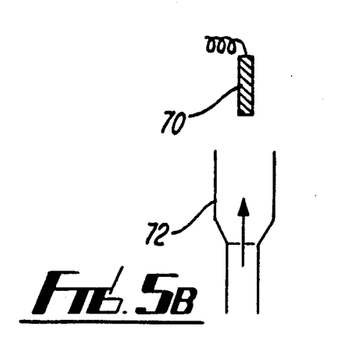

FIG. 5A shows a fume monitoring system in which a piezoelectric sensor crystal 70 is horizontally mounted above a fluidized bed 72, while FIG. 5B shows a similar monitoring system in which the sensor 70 is vertically mounted above the fluidized bed 72.

Figure 6:
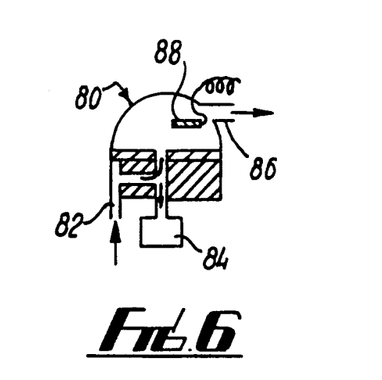

FIG. 6 shows a dust-separating cyclone head 80 having an inlet duct 82 fed with a stream of dusty air. The cyclone head 80 acts in a known manner to separate heavier particles out of the incoming air-stream, and to drop them into a lower receptacle 84. Air which now contains substantially only the lighter particles of dust passes up through the top of the cyclone head 80 to be exhausted through an outlet duct 86. Light dust in this exhaust stream is monitored by a piezoelectric sensor 88 mounted within the cyclone head 80 just upstream of the outlet duct 86. A suitable arrangement of the cyclone head 80 will enable the sensor 88 to be exposed substantially only to dust particles which are small enough to be respirable, and which therefore present a particular health hazard.

Figure 7:
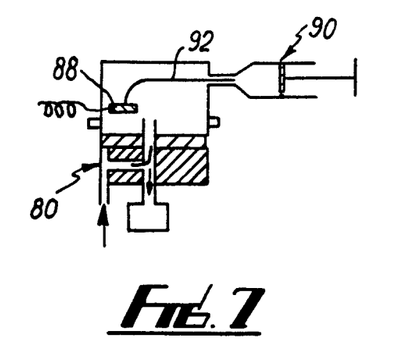

FIG. 7 represents a modification of the FIG. 6 system in which the cyclone head 80 is provided with a viewing window. Also, the sensor 88 is provided with an air jet cleansing system 90 which is schematically depicted as a manually-operable syringe feeding through a conduit 92 to a nozzle tip positioned to blow dust off the sensor 88 when this function is required. (Note: in practice an automatic microprocessor controlled air jet, vacuum or solvent cleansing system is used, FIG. 9, employing solenoid valves).

Figure 8:
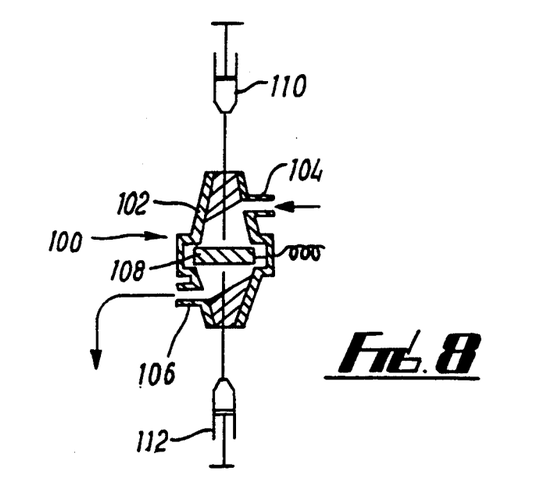

FIG. 8 shows a more advanced model of respirable dust monitor 100 which is intended to be used in conjunction with a cyclone head (not shown) having an inner aluminium dust capture chamber and Millipore filter (a proprietary membrane filter). The monitor 100 has a double-ended chamber 102 with an upper inlet duct 104 and a lower outlet duct 106. A piezoelectric dust sensor crystal 108 is horizontally mounted in the center of the chamber 102 so as to be exposed to the stream of (potentially) dust-carrying gas passing through the chamber 102 from the inlet 104 to the outlet 106.

The monitor 100 is provided with a sensor cleaning system schematically depicted as an upper syringe 110 and a lower syringe 112. Operation of the syringes 110 and 112 will air-blast the upper and lower surfaces of the sensor crystal 108 respectively, to remove dust or other particles accumulated thereon. (Note: again the automatic system above replaces this system in practice).

The outlet duct 106 may be coupled to a downstream filter (not shown) for cross-checking and calibration of the dust monitor 100.

Figure 9:
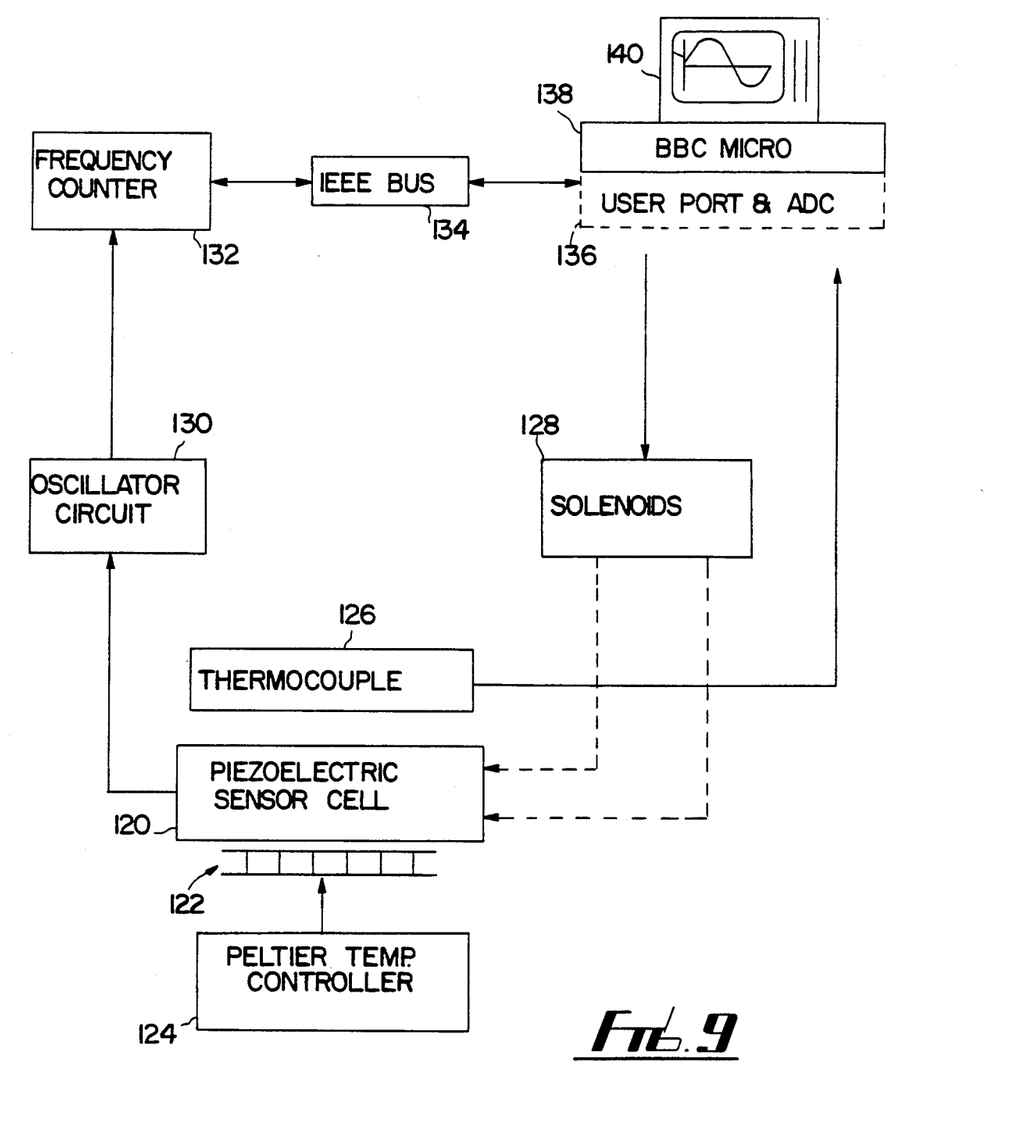

FIG. 9 is a block schematic diagram of a computerised dust monitoring system based on a piezoelectric sensor cell 120 which may be in the form of a dust sampling cell as shown in any of FIGS. 1 to 8, or in any other suitable form. The piezoelectric sensor within the cell 120 has its temperature stabilised by a Peltier unit 122 under the control of a Peltier temperature controller 124 and a temperature-sensing thermocouple 126.

Dusty air (or potentially dusty air) is periodically fed to the sensor cell 120, alternately with clean air for sensor-cleaning purposes, under the control of air-stream changeover solenoids 128.

The piezoelectric sensor within the sensor cell 120 is connected to an external electronic oscillator circuit 130 whose oscillatory frequency is determined by the resonant frequency of the piezoelectric sensor, as modified by the accretion of dust or other particulate material on the sensor. The output frequency of the oscillator circuit 130 is measured by a frequency counter 132, and the frequency measurement is transferred via an IEEE bus (data communications link) 134 to the port 136 of a microcomputer 138 (in this instance, a BBC Micro). The port 136 also links the microcomputer 138 to the solenoids 128 for their programmed control, and to the thermocouple 126 for the reception of temperature correction signals.

The microcomputer 138 calculates the density of air-borne dust in any suitable manner on the basis of changes in the resonant frequency of the piezoelectric sensor within the sensor cell 120, and displays the calculation results in a suitable form, for example on a linked VDU 140.

Figure 10:
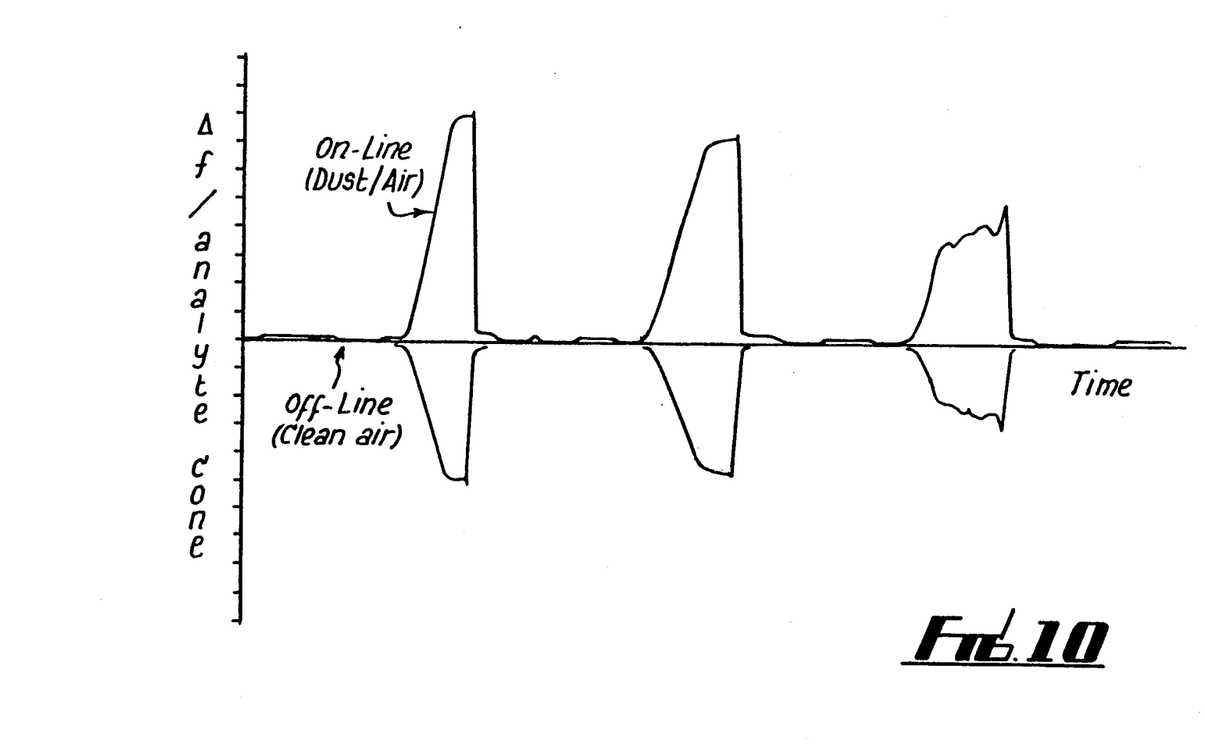

FIG. 10 shows typical graphical results obtainable by dust monitoring in accordance with the invention. The vertical scale of the lower graph shows the progressive decrements in the resonant frequency of the piezoelectric sensor during three successive periods of exposure to dust-laden air, the horizontal scale being time. (In this instance, use is made of cellulose dust generated in a fluidised bed). The vertical scale of the upper graph shows the corresponding concentration of air-borne dust (in millgrammes per cubic meter) to the same horizontal time scale. The central horizontal line is the zero or datum level corresponding to clean (dust-free) air. The graphs of FIG. 10 could be displayed on the V.D.U. 140 of the FIG. 9 computerised dust monitoring system, and the microprocessor 138 could be programmed to display either or both of the FIG. 10 graphical plots. Either the rate of change (slope of the graphical plot) can be monitored to measure the rate of dust accumulation on the sensor, or the integrated total per unit time (area between the graphical plot and the zero line per sampling period) can be monitored to give an equivalent result, or both these values may be monitored simultaneously.

Figure 11:
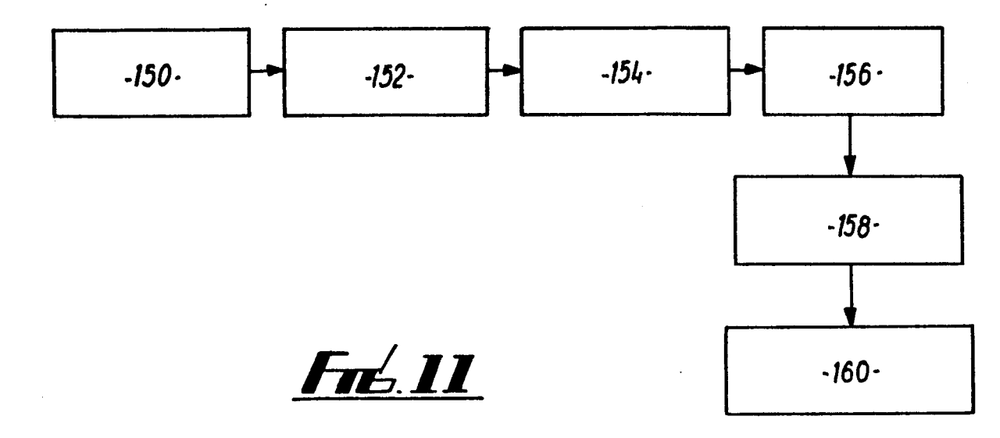

FIG. 11 is a block circuit diagram of an electronic circuit for measuring the resonant frequency of a piezoelectric dust sensor (e.g. as previously described, or any other suitable type), and for responding to a change (decrease) in resonant frequency above a certain magnitude to give an alarm signal indicative of an excessive concentration of dust. The FIG. 11 circuit comprises an oscillator circuit 150 whose frequency-determining element is the piezoelectric dust sensor, a frequency prescaler 152 to divide the output frequency from the oscillator 150 to a more convenient value, a frequency-to-voltage converter 154 to convert the scaled frequency to a proportionate analogue voltage, a smoothing circuit 156 to minimize undesirable ripple and transients, a differential amplifier 158 set to produce an output when the smoothed frequency-dependent voltage changes by more than a predetermined limit, and an audio and/or visual alarm circuit 160 driven or triggered by the output from the differential amplifier 158.

Figure 12:
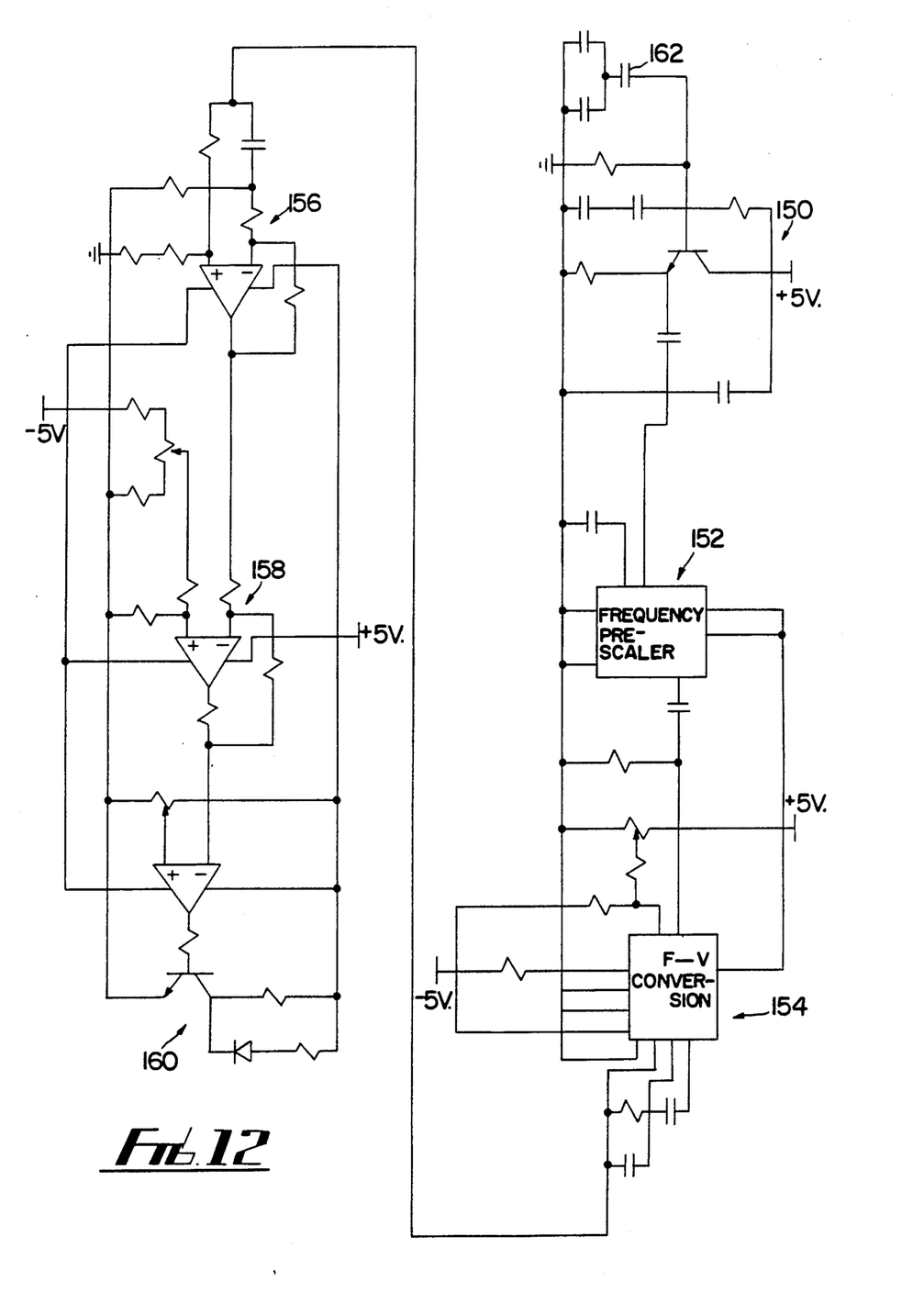

FIG. 12 shows the FIG. 11 circuit in detail, and portions of the FIG. 12 circuit that correspond to the functional blocks of the FIG. 11 circuit are identified by the same reference numerals. Additionally, in the FIG. 12 circuit the reference numeral 162 denotes the frequency-determining piezoelectric dust sensor.

The circuit of FIG. 12 can be miniaturised and battery-powered, and utilised in conjunction with a suitable air sampling system to form a personal dust monitor that can be carried (e.g. attached to clothing) by a person who may be exposed to undesirably high levels of air-borne respirable dust. In such a case, the FIG. 12 circuit would be present to give an alarm at the appropriate TLV level, i.e. the desirable or mandatory threshold limiting value OES and MEL (occupational exposure standard and maximum exposure level) corresponding to the maximum concentration of dust to which a worker can be safely or legally exposed in a given period, for example, and 8-hour working day.

Figure 13:
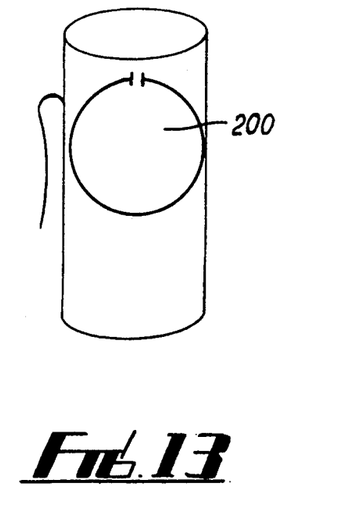

If a levelling device is incorporated in the apparatus by using a gas or liquid supported floating sphere ball device 200, FIG. 13, the device can be made to be affected as little as possible by movements of the wearer. A simpler device could incorporate a pendulum supported by a ball joint which would allow the device to remain level over a small degree of angular variation of the apparatus as a whole. Such devices could, in addition to being attachable to a users clothing, be attached to a safety helmet or safety classes.

Figure 14:
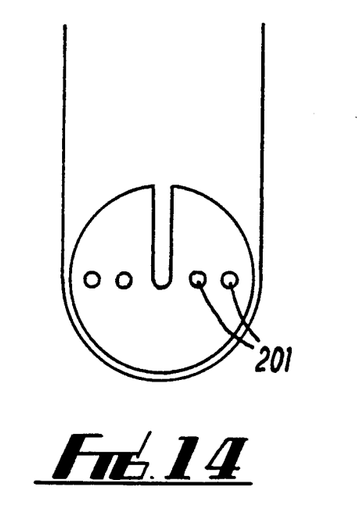

In the gas supported version suitable air outlets 201 can be provided to produce a cushion of air around the ball device 200 as illustrated in FIG. 14. As an added refinement a microchip tilt detector can be included for monitoring any actual movement away from the horizontal and to provide a default signal on detecting tilt beyond a present limit.

The sensitivity of dust detection is proportional to the reciprocal of the area of the piezoelectric sensor that is exposed to dust. Typical theoretical values of resonant frequency decrement are 240 Hertz per microgramme of dust for an exposed sensor area of 1 centimeter diameter, and 667 Hertz per microgramme of dust for an exposed sensor area of 6 millimeters diameter. (Those figures apply to sensors that are coated with a binder to cause adherence of dust during monitoring). These dust detection sensitivities may be translated to respective detection limits of 1 milligramme of dust per cubic meter of air and 400 microgrammes of dust per cubic meter of air using an air sampling flow rate of 10 liters per minute and one-minute sampling periods. The calculated detection limits are based on a ($3 \times sigma$) noise level of plus or minus 2.5 Hertz. Lower detection limits are possible with a smaller area of piezoelectric sensor exposed to the dust and/or with higher air sampling flow rates.

Further figures relating sensor area to sensitivity and detection limits are as follows:

Diameter of exposed area = 3.0 millimeters (corresponding to an exposed area of 0.0707 square centimeters) gives a sensitivity of 2669 Hertz per microgramme of dust or 400 picogrammes of dust per Hertz, as calculated from the previously cited Sauerbrey equation. The corresponding detection limit is 1.1 nanogrammes, calculated from ($3 \times sigma$)/sensitivity (where sensitivity is expressed as Hertz per microgramme), taking sigma as 1 Hertz (being the piezoelectric sensor crystal loading detection limit).

With calculations made on the same basis as quoted above, an exposed area with a diameter of 10.6 millimeters (corresponding to an exposed area of 0.7854 square centimeters) gives sensitivity of 240 Hertz per microgramme of dust or 4 nanogrammes of dust per Hertz, and a detection limit of 13 nanogrammes.

Again on the same basis, an exposed area with a diameter of 13.86 millimeters (corresponding to an exposed area of 1.5087 square centimeters) gives a sensitivity of 125 Hertz per microgramme of dust or 8 nanogrammes of dust per Hertz, and a detection limit of 24 nanogrammes.

The above detection limits based on area of piezoelectric sensor exposed to dust can be converted to detection limits under the dynamic conditions of exposure to flowing air by dividing the area-dependent detection limit by the product of the air flow rate and the signal update time (or sampling period), and multiplying by a suitable conversion constant whose magnitude depends on the relevant units of measurement.

Thus the 3.0 millimeter diameter case referred to above, with a signal update time of 1 second and a flow rate of 10 liters per minute, gives a dynamic detection limit of 7 microgrammes of dust per cubic meter of air. Similarly, the 13.86 millimeter diameter case referred to above, with a signal update time of 1 second and a flow rate of 50 milliliters per minute, gives a dynamic detection limit of 29 milligrammes of dust per cubic meter of air.

While the monitors and monitoring procedures described above have particularly referred to dusts and other such particulate materials, the apparatus and method of the invention can also be applied to the detection and monitoring of gas-borne and air-borne biological substances and micro-organisms. For use as a biosensor, the piezoelectric crystal or other form of piezoelectric sensor would be coated with an agar rich in nutrients to encourage growth of the selected micro-organism. Alternatively, use may be made of a coating which reacts directly with some side product chemically related to a specific organism. Unlike the seconds or minutes that would be typical for dust monitoring, bisensors may require a response time of several hours. Biosensor response time could be reduced by providing optimum biological growth conditions at the detection surface of the piezoelectric sensor and in the sampling chamber; such optimum growth conditions may include correct humidity, temperature, pH of the agar, and improved growth nutrients for specific organisms. Alternatively, a second piezoelectric sensor may be mounted downstream of the piezoelectric biosensor, with the second sensor being coated to detect specific respiratory gases emitted by the micro-organism being cultivated on the first (upstream) sensor.

The apparatus and method of the invention may be utilised in any situation where health and safety, and/or product quality require to be protected against airborne dusts, particulate materials, and/or micro-organisms. The apparatus and method of the invention may also be utilised for detecting and measuring airborne dusts, particulate materials, and/or micro-organisms in circumstances where health is not an issue; for example, in scientific and technical studies, and in the control of totally enclosed processes.

Without prejudice to the generality of the above-mentioned potential applications of the present invention, it is envisaged that the invention may be utilised in the following industrial contents:

(1) industrial food preparation and processing;
(2) mining and quarrying;
(3) building;
(4) industrial manufacture of chemicals, paints, solvents, and the like;
(5) iron and steel foundries;
(6) farms, agriculture, and horticulture;
(7) semiconductor fabrication;
(8) "clean rooms" for scientific and medical purposes;
(9) textile industries;
(10) cement works, brick works, and the like.

The above describes various basic embodiments of dust monitors and their applications and there now follows a brief summary of a possible development of the Casella Cyclone Dust Personal Monitor.

The apparatus as described can be utilised to provide modification to the Casella Cyclone Dust Personal Monitor by replacement of the standard millipore filter paper by a rimbound or free hanging piezoelectric crystal integrated with an oscillator drive circuit. This can be set up to provide an electronic readout of dust in dynamic real-time rather than time-averages retrospective result. The arrangement can also include a set voltage audio-visual trigger linked system with occupational exposure standards (OES) and maximum exposure levels (MEL) of dust which allows a dust profile history for each working day to be stored onboard a microchip and later dumped to a micro or mainframe computer for a health records management system. The arrangement can be adapted to a stationary multipoint dust monitor for overall building/factory management from a central computer control point and can be linked to an event marker either manually or via radio pick-up for routine sites around the building.

Several different receivers can be produced and these are:

(a) single crystal system with limited detection limits related to temperature and humidity range of operating conditions.
(b) double crystal humidity compensated system.
(c) triple crystal humidity and temperature compensated system for ug detection limits, either respirable or alternatively general dust.
(d) double crystal respirable and general dust system with limited detection limits.
(e) quadruple crystal with humidity, temperature, compensation for respirable and general dust, with ug detection limits.
(f) double crystal system with alternate measurement switching between general dust and humidity measurement on crystal A and respirable dust and temperature on crystal B.

Figure 15:
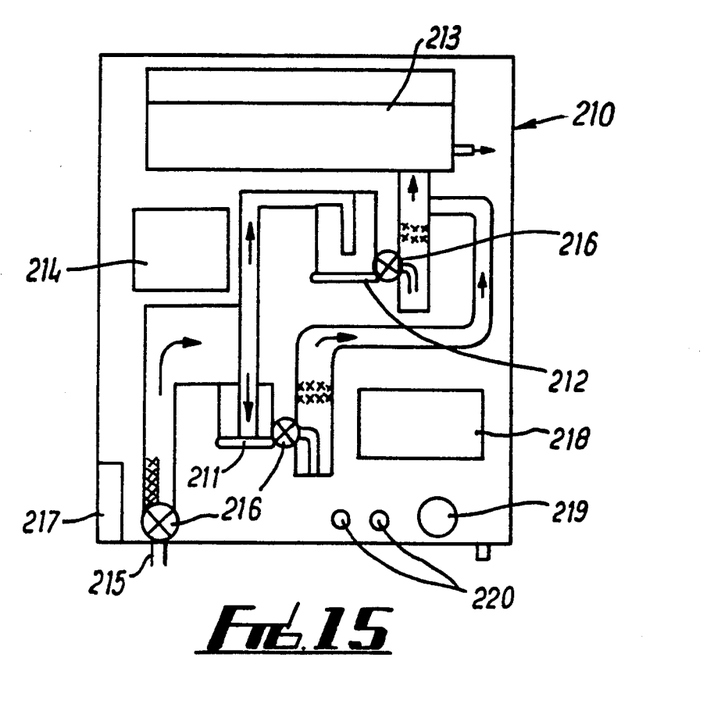

An example of (f) above is illustrated in FIG. 15. The device is enclosed in a casing 210 and incorporates two crystals 211 and 212. The casing also encloses a battery system and pump unit 213 and an oscillator circuit 214. An inlet vent 215 is provided and a number of solenoids 216 control the air flow. Crystal 211 is used to measure general dust and humidity alternately and crystal 212 is used to measure respirable dust and temperature alternately.

The device also incorporates a tilt mechanism 217, data logger and display device 218 together with audio 219 and visual 220 indicators.

A further modification to the Casella system provides that the dust cell is controlled to sample on, or crystal vacuum clean via microsolenoid valves; this allows the dust cell containing the piezoelectric crystal to be vacuum cleaned.

The system can provide rapid sensor response times over periods of a few seconds if required. Dust can be retained at the crystal surface by the following means: stationary phase films, polymeric charged films (coatings), magnetic coatings, gravity.

Further the perturbation (disruption) noise signal generated by the presence of dust particles in the vicinity of an oscillating crystal intergrated with a tuned circuit, can be used as an alternative method of data measurement and interpretation of dust levels being monitored.

Other standard signal treatment includes frequency subtraction (F) frequency divide (ratioing). The piezo dust monitor uses rate of signal change as its principle mode of relating dust concentration in the atmosphere. It can also give a total dust exposure over sampled time period.

While certain modifications and variations have been made described above, the invention is not restricted thereto, and other modifications and variations can be adopted without departing from the scope of the invention.

We claim:

1. A dust monitor comprising a piezoelectric sensor including a piece of piezoelectric material and an electrode system thereon, and exposure means to expose the piezoelectric sensor at least periodically to a stream of a gas which may contain dust or other organic or inorganic particulate material whose presence in or absence from the gas is to be monitored wherein the exposure means comprises a dust size discriminator which cause substantially only particles of repirable size to reach the piezoelectric sensor and diverts larger particles to a second piezoelectric sensor.

2. A dust monitor as claimed in claim 1, wherein the piezoelectric material comprises a quartz crystal rim bound within a sample chamber of the dust monitor, and incorporating temperature stabilisation means comprising means to supply a stream of temperature-controlled air to a portion of the piezoelectric sensor other than the portion or portions of the piezoelectric sensor exposed to the stream of gas whose particulate content is to be monitored so as to tend to stabilise the temperature of the sensor during operation of the dust monitor.

3. A dust monitor as claimed in claim 1, wherein the piezoelectric material comprises a quartz crystal rim bound within a sample chamber of the dust monitor and incorporating a stabilisation means comprising a Peltier pile thermally coupled to the piezoelectric sensor and supplied in use with current of a magnitude and polarity such as to stabilise the temperature of the piezoelectric sensor within a predetermined range of temperatures.

* * * * *

UNITED STATES PATENT AND TRADEMARK OFFICE
CERTIFICATE OF CORRECTION

PATENT NO. : 5,056,355
DATED : October 15, 1991
INVENTOR(S) : Michael J. Hepher et al It is certified that error appears in the above-identified patent and that said Letters Patent is hereby corrected as shown below:

On the title page, item [73] Assignee, should read as follows:

--[73] Assignee: Glasgow College Enterprises Limited, Glasgow, Scotland--.

Signed and Sealed this

Sixth Day of October, 1992

Attest:

DOUGLAS B. COMER

*Attesting Officer*       *Acting Commissioner of Patents and Trademarks*